United States Patent [19]

Katsumoto

[11] 4,001,274
[45] Jan. 4, 1977

[54] RECOVERY OF 2-PYRROLIDONE FROM AQUEOUS SOLUTIONS

[75] Inventor: Kiyoshi Katsumoto, El Cerrito, Calif.

[73] Assignee: Chevron Research Company, San Francisco, Calif.

[22] Filed: Nov. 28, 1975

[21] Appl. No.: 635,996

[52] U.S. Cl. .................................... 260/326.5 FN
[51] Int. Cl.² ..................................... C07D 207/12
[58] Field of Search .......... 260/326.5 FN, 239.3 A

[56] References Cited

UNITED STATES PATENTS

| | | | |
|---|---|---|---|
| 3,016,287 | 1/1962 | Hopkins et al. | 260/239.3 A X |
| 3,806,427 | 4/1974 | Geruasi et al. | 260/326.5 FN X |

*Primary Examiner*—Donald G. Daus
*Assistant Examiner*—D. B. Springer
*Attorney, Agent, or Firm*—G. F. Magdeburger; Dix A. Newell; S. Russell LaPaglia

[57] ABSTRACT

2-pyrrolidone is separated from aqueous solution by phase separation in the presence of potassium hydrogen phosphate.

6 Claims, No Drawings

RECOVERY OF 2-PYRROLIDONE FROM AQUEOUS SOLUTIONS

BACKGROUND OF THE INVENTION

The recovery of 2-pyrrolidone from aqueous solution is inherently difficult because of the hydrophilic character of this lactam, a 5-membered ring of the formula:

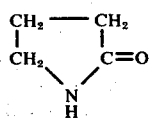

In the polymerization of 2-pyrrolidone using an alkaline catalyst, the recovery of unreacted monomer can be accomplished by washing the polymerization reaction mixture with water, or another 2-pyrrolidone miscible solvent, to extract the unreacted 2-pyrrolidone and the alkaline catalyst. The resultant alkaline aqueous 2-pyrrolidone solution may be directly distilled. However, prolonged exposure to alkaline aqueous solutions under distillation conditions can hydrolyze the sensitive 2-pyrrolidone ring thereby depressing the yield of 2-pyrrolidone.

Concentrated acidic aqueous solutions of higher lactams, such as caprolactam, have been found to separate upon neutralization with hydroxides or alkali metal carbonates (see U.S. Pat. Nos. 2,313,026, 2,579,851 and 2,667,483). U.S. patent application Ser. No. 224,284, filed Feb. 7, 1972, teaches that among sodium and potassium salts including the chloride, sulfate, carbonate, nitrate, acetate and thiocyanate, only the carbonate separates aqueous 2-pyrrolidone solutions.

SUMMARY OF THE INVENTION 2-pyrrolidone is recovered from an aqueous solution by a process including the step of adding to the solution potassium hydrogen phosphate in an amount sufficient to cause a separation of the solution into two liquid phases, one of which contains substantially more 2-pyrrolidone than the other.

DETAILED DESCRIPTION OF PREFERRED EMBODIMENTS

While 2-pyrrolidone is completely miscible with water, alcohols, esters, ketones and other hydrophilic solvents, it is found to be recoverable from aqueous solutions containing a solvent selected from the group consisting of water and mixtures of water and a hydrophilic solvent, by addition of potassium hydrogen phosphate in an amount sufficient to cause separation of the solution into two liquid phases. One liquid phase is the 2-pyrrolidone-containing phase which contains water, a small amount of phosphate, and substantially more 2-pyrrolidone than the other phase. In fact, this phase may contain substantially all the 2-pyrrolidone present in the original solution. The other phase is the phosphate-containing phase which contains water, a small amount of 2-pyrrolidone and substantially more of the phosphate than the 2-pyrrolidone-containing phase. In fact, this phase may contain substantially all the phosphate added to the original solution.

The phosphate added to effect separation of the aqueous 2-pyrrolidone solution is potassium hydrogen phosphate, $K_2HPO_4$. Potassium hydrogen phosphate is added in amount sufficient to effect separation of an aqueous 2-pyrrolidone solution such that substantially more 2-pyrrolidone is contained in one phase than the other. The following preferred amounts correspond to a final solution temperature of about 15°–100° C, and preferably about 20°–30° C. Preferably, to an aqueous solution comprising less than 50 weight percent 2-pyrrolidone, potassium hydrogen phosphate is added in an amount sufficient to make a final solution comprising about 5–50 weight percent $K_2HPO_4$. Preferably, to an aqueous solution comprising less than 60 weight percent but more than 30 weight percent 2-pyrrolidone, potassium hydrogen phosphate is added in an amount sufficient to make a final solution comprising about 1–40 weight percent $K_2HPO_4$. Preferably, to an aqueous solution comprising more than 50 weight percent 2-pyrrolidone, potassium hydrogen phosphate is added in an amount sufficient to make a final solution comprising about 0.5–30 weight percent $K_2HPO_4$. In each case, the final solution separates into two liquid phases, one of which contains substantially more 2-pyrrolidone than the other.

The process of the present invention is effective in separating even dilute aqueous solutions of 2-pyrrolidone. By dilute solutions is meant solutions containing less than about 30 weight percent 2-pyrrolidone based on the solution weight before the addition of phosphate. The present process is effective in recovering 2-pyrrolidone even from solutions containing less than 10 weight percent 2-pyrrolidone.

The aqueous 2-pyrrolidone solution may initially contain any alkaline material, such as any of the alkaline materials proposed as alkaline polymerization catalysts for the polymerization of 2-pyrrolidone. Such alkaline materials include the hydroxides of the alkali metals, such as potassium hydroxide and sodium hydroxide, and organic bases such as quaternary ammonium hydroxides, e.g. tetra (lower alkyl) ammonium hydroxides. The solvent employed in the aqueous solution of 2-pyrrolidone may be any of the usual solvents for 2-pyrrolidone and such solvents include water, or mixtures of water and hydrophilic solvents, such as alcohols. Less preferably, the phosphate may be formed in situ to the extent of the amount of base present by the addition of the corresponding acid to the alkaline solution, e.g. by the addition of ortho phosphoric acid, $H_3PO_4$. The total salt used to effect separation may comprise, in addition to the aforementioned phosphate, potassium carbonate, $K_2CO_3$, in amounts of 1–10 weight percent of the final solution. The carbonate may be added directly or may be formed in situ by the addition of carbon dioxide to the alkaline aqueous solution of 2-pyrrolidone. However, it is usually more convenient to add the needed amounts of phosphate or carbonate directly to the solution to effect separation at a given concentration.

Substantially all the 2-pyrrolidone originally present in the aqueous solution may be contained in the 2-pyrrolidone-containing phase after phase separation. The 2-pyrrolidone is easily recovered by mechanically isolating the 2-pyrrolidone-containing phase and removing the remaining water, or other solvents from it by distillation, preferably by vacuum distillation. The 2-pyrrolidone-containing phase is easily isolated by any conventional mechanical means, such as decantation. Distillation of residual water in the 2-pyrrolidone-containing phase is carried out by the usual methods, or water may be removed by other means such as by the use of a drying agent. Preferably, the phosphate which was added to the aqueous solution to cause separation is recovered by evaporating the solvent from the phosphate-containing phase. The phosphate may be recycled.

EXAMPLES

EXAMPLE 1

To a solution of 17.5 g of 2-pyrrolidone and 35 g of water (33 weight percent 2-pyrrolidone) was added 50 g of $K_2HPO_4$ (sufficient phosphate to make a final solution comprising 49 weight percent $K_2HPO_4$). The mixture was shaken in a separatory funnel and the phases were allowed to separate at room temperature into an upper 2-pyrrolidone-containing aqueous phase (23 g) and a lower phosphate-containing aqueous phase (49.5 g). The upper phase was isolated and analyzed for 2-pyrrolidone by gas chromatography. It was found to contain 17.2 g of 2-pyrrolidone corresponding to 98 percent recovery of 2-pyrrolidone from the original solution. Potassium analysis of the upper phase showed it contained only 0.07 g of $K_2HPO_4$.

EXAMPLE 2

To an aqueous solution of the same proportions as in Example 1 was added 30 g of $K_2HPO_4$ (sufficient $K_2HPO_4$ to make a final solution comprising 36 weight percent $K_2HPO_4$). The mixture was shaken in a separatory funnel and the phases were allowed to separate at room temperature into an upper 2-pyrrolidone-containing phase (26.4 g) and a lower phosphate-containing phase. The upper phase was separated and analyzed. It contained 15.3 g of 2-pyrrolidone (87 percent recovery) and 0.13 g of $K_2HPO_4$.

EXAMPLE 3

An aqueous solution of the same proportions as in Example 1 was saturated with sodium borate and shaken in a separatory funnel at room temperature. No liquid-liquid phase separation was observed.

What is claimed is:

1. A process for recovering 2-pyrrolidone from an aqueous solution, which includes the step of adding to the solution potassium hydrogen phosphate in an amount sufficient to cause separation of the solution into two liquid phases, one of which contains substantially more 2-pyrrolidone than the other.

2. A process for recovering 2-pyrrolidone from an aqueous solution comprising less than 50 weight percent 2-pyrrolidone, which includes the step of adding to the solution potassium hydrogen phosphate in an amount sufficient to make a final solution comprising about 50–50 weight percent potassium hydrogen phosphate.

3. A process for recovering 2-pyrrolidone from an aqueous solution comprising less than about 60 weight percent but more than about 30 weight percent 2-pyrrolidone, which includes the step of adding to this solution potassium hydrogen phosphate in an amount sufficient to make a final solution comprising about 1–40 weight percent potassium hydrogen phosphate.

4. A process for recovering 2-pyrrolidone from an aqueous solution comprising more than about 50 weight percent 2-pyrrolidone, which includes the step of adding to the solution potassium hydrogen phosphate in an amount sufficient to make a final solution comprising about 0.5–30 weight percent potassium hydrogen phosphate.

5. A process according to claim 1 wherein said aqueous solution is an alkaline aqueous solution containing an alkali metal hydroxide or carbonate, or a quaternary ammonium hydroxide.

6. A process for recovering 2-pyrrolidone from an aqueous solution which includes the steps of adding to the solution potassium hydrogen phosphate in an amount sufficient to cause separation of the solution into two liquid phases, isolating the phase containing the most 2-pyrrolidone, and recovering the 2-pyrrolidone from said phase.

* * * * *